United States Patent [19]

Czapla et al.

[11] Patent Number: 5,783,190
[45] Date of Patent: Jul. 21, 1998

[54] *BUCHLOE DACTYLOIDES* EXTACTS HAVING INSECTICIDAL PROPERTIES

[75] Inventors: Thomas H. Czapla, Urbandale; Scott A. Mundell, West Des Moines; Nandha Kumar Balasubramanian, Des Moines, all of Iowa

[73] Assignee: Pioneer Hi-Bred International, Inc., Des Moines, Iowa

[21] Appl. No.: 653,787

[22] Filed: May 28, 1996

[51] Int. Cl.$^6$ ............................................. A61K 35/78
[52] U.S. Cl. ............................................. 424/195.1
[58] Field of Search ..................................... 424/195.1

[56] References Cited

PUBLICATIONS

Belitz et al., Z. Lebennsm. Unters.–Forsch 714: 442–446 (1982).
Christeller et al., Insect Biochem. 19: 233–241 (1989).
Hilder et al., Nature 330: 160–163 (1987).
Johnson et al., Proc. Natl. Acad. Sci. 86: 9871–9875 (1989).
Laemmli, Nature 227: 680–685 (1970).
Czapla et al., J. Econo. Ento. 83(6): 2480–2485 (1990).

*Primary Examiner*—Jean C. Witz

[57] ABSTRACT

The invention comprises a substances or plurality of substances extracted from the seeds of buffalo grass, *Buchloe dactyloides*. The crude extract was found to comprise one or a plurality of substances having molecular weights of less than 20 kDa which are natural insecticides against corn rootworm. Bioassays show corn rootworm mortality of up to 100% when larvae are fed a diet containing crude or purified buffalo grass extract.

10 Claims, 7 Drawing Sheets

BUCHLOE DACTYLOIDES EXTACTS HAVING INSECTICIDAL PROPERTIES

FIELD OF THE INVENTION

The invention relates to methods and materials for controlling insect species. In particular, the invention relates to substances extracted from the plant *Buchloe dactyloides*, buffalo grass, which exhibit insecticidal activity.

BACKGROUND OF THE INVENTION

Numerous insect species are serious pests to common agricultural crops such as corn, soybeans, peas and similar crops. During the last century, the primary method of controlling such pests has been through the application of synthetic chemical insecticide compounds. However, as the use of such chemical compounds proliferated and continued, it became evident that such wide-spread use posed problems with regard to the environment, the non-selectivity of the compounds, increasing insect resistance to the chemicals and the effect of such compounds, after run-off, on higher order species such as fish and birds among others. As a result of such problems, other methods of controlling insect pests were sought and tried.

One such alternative method of pest control has been the use of biological organisms which are "natural predators" of the species sought to be controlled. Such predators may include other insects, fungi (milky-spore) and bacteria such as *Bacillus thurengiensis* cv. Alternatively, large colonies of an insect pest have been raised in captivity, sterilized and released into the environment in the hope that mating between the sterilized insects and fecund wild insects will decrease the insect population. While both these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off a plant or removed from a treated area by rain. Consequently, while the use of such biological controls has desirable characteristics and has met with some success, in practice these methods seem severely limited. However, recent scientific advances seem to offer new and different opportunities for controlling insect pests.

The advances in biotechnology in the last two decades have presented new opportunities for pest control through genetic engineering. In particular, advances in plant genetics coupled with the identification of insect growth factors and naturally occurring plant defensive substances, compounds or agents offer the opportunity to create transgenic crop plants capable of producing such defensive agents to thereby protect the plants against insect attack.

Scientists have identified some specific plant components or compounds which act as defensive agents to protect a plant from attack by insect pests and pathogens. While such components are usually present at only low levels in various plant tissues, some of them are also capable of being induced to higher levels upon attack by an insect pest or a pathogen. Examples of such defensive compounds include alkaloids, terpenes and various proteins such as enzymes, enzyme inhibitors and lectins. Of particular interest are compounds which can inhibit insect growth or kill the insects while they are growing. One example of such a compound to be inhibited is trypsin, a digestive enzyme secreted by the midget cell into the endo and exo peritrophic space. Trypsin inhibitors are known in the art, and a brief discussion of them will serve to illustrate the advances being sought and the significance of the invention disclosed herein.

The role of trypsin is to hydrolyze polypeptides into smaller units which can then be utilized by the host subject, for example, an insect. An enzyme such as trypsin which catalyzes the hydrolysis of peptide bonds is called a protease. If trypsin activity is blocked, insect growth may be inhibited. A trypsin inhibitor (abbreviated TI) is thus a compound, typically a protein compound, which will block or decrease trypsin protease activity. As a result of such blockage or decrease in trypsin protease activity, a host subject which has ingested a trypsin inhibitor with its food may fail to grow, mature and may indeed ultimately starve and die.

Currently, agricultural biochemical research is seeking compounds which, when transgenically inserted into food crops, will provide the crops with increased insect protection by increasing the mortality rate of insects which feed upon such crops. For example, Hilder et al. (3) introduced the Bowman-Birk trypsin inhibitor gene from cowpeas into tobacco plants and showed that the transgenic plants were able to resist damage from a lepidopteran insect. Transformation and expression of other trypsin inhibitor genes such as potato trypsin inhibitor I and II also resulted in transgenic plants which showed resistance to insect attack. However, transgenic plants which contained an unexpressed trypsin inhibitor gene were susceptible to insect attack (4). Consequently, in order to have pest protection, a plant must not only contain the protective gene, but it must also express it. That is, the trypsin inhibitor gene must be producing, or capable of producing upon pest attack, the inhibitor or defensive agent.

The choice of inhibitor or other insecticidal compound to be transgenically inserted into a plant species is crucial to effective pest control. For example, Belitz et al. (1) and Christeller et al. (2) have shown that trypsin inhibitors obtained from different plant species have considerably different inhibition constants ($K_i$ values). Consequently, prior to genetic transformation of a crop species, it was found necessary to screen trypsin inhibitors from a variety of plant sources in order to identify those having sufficiently strong activity so that the transgenic crop plant will have sufficient resistance to insect attack. For purposes of identifying such trypsin inhibitors, it is noted that except for inducible inhibitors, most natural inhibitors are located in plant storage organs such as seeds and tubers.

Plant species from throughout the globe have been and are being investigated for potential insecticidal compounds which can be transgenically bioengineered into valuable agricultural crops and plants to thereby give such plants protection against insect attack. While the most widely publicized and popular source of compounds has been tropical rain forest plants, native North American plants are also being investigated. One such native plant which has not been previously investigated or tested is *Buchloe dactyloides* (buffalo grass, hereinafter also designated as *B. dactyloides* or BG).

The purpose of the present invention is to identify and characterize one or a plurality of insecticidal substances obtainable from *B. dactyloides*, which substances reduce insect growth and/or increase insect mortality.

It is a further purpose of the invention to provide a method for the separation and isolation of one or a plurality of substances obtainable from *B. dactyloides* and to demonstrate the inhibitory and/or insecticidal nature of such substances.

It is a further purpose of the invention to provide one or a plurality of *B. dactyloides* substances as described herein which have sufficient insect growth inhibitory effects or insecticidal properties to warrant the gene or genes expressing such substances being transgenically inserted into a food crop gene where they may be expressed and may provide protection against one or a plurality of insect species including, but not limited to, European corn borer (*Ostrinia nubilalis*), Diabrotica species such as the Western, Southern and Northern corn rootworms, corn earworm (*Helicoverpa zea*), cowpea weevil (*Callosobruchus maculatus*) and similar insect pests known to those skilled in the art.

It is a further purpose of the invention to provide one or a plurality of of *B. dactyloides* substances which can be applied, alone or in combination with a carrier according to methods known to those skilled in the art, to a plant species such that the substances or substances topically remain on the plant or are systemically taken up by the plant species.

SUMMARY OF THE INVENTION

The invention identifies and provides one or a plurality of insecticidal substances, or mixture thereof, obtainable from *Buchloe dactyloides*, said substances having a molecular weight less than 20 kilodaltons (kDa), wherein the preferred substance(s) have a molecular weight less than 8 kDa and the most preferred have a molecular weight less than 5 kDa.

The invention provides for extracting a substance or a plurality of substances from *Buchloe dactyloides*, buffalo grass, which can be used as a insecticide in either a crude extract form or in a purified form as described herein. Either the crude or the purified substances extracted from buffalo grass can be applied to plants topically, for example, by spraying a solution containing said substance(s), or systemically, for example, by admixing said substance(s) in a suitable carrier formulation such as known to those skilled in the art and applying the formulation containing said substance(s) to plants.

The invention is also directed to one or a plurality of purified insecticidal compounds, or mixture thereof, obtained from *Buchloe dactyloides*, said invention comprising the steps of extracting powdered or sliced seeds from said *Buchloe dactyloides*, extracting said powdered or sliced seeds with aqueous solution to obtain a crude extract and purifying the crude extract by chromatographic instrumental techniques to obtain one or a plurality of insecticidal proteins or compounds having a molecular weight less than 8 kDa and preferably less than 5 kDa.

The invention is further directed to a process for protecting plants against insect attack by corn rootworms, European corn borer (*Helicoverpa zea*), and similar insects comprising exposing said insects to one or a plurality of insecticidal substances obtained from *B. dactyloides*, said insecticidal substances being contained within a crude or purified extract of *B. dactyloides* seed and identified as having one or a plurality of active substances whose molecular weights are less than 8 kDa; wherein a plurality of substances of molecular weight less than 5 kDa are the preferred insecticidal substances.

BRIEF DESCRIPTION OF THE DRAWINGS

FIG. 1 illustrates the percentage mortality of corn rootworm larvae treated with buffalo grass extract fractions obtained according to the invention using a Bio-Rad Rotofor Isoelectric Focusing apparatus, and the pH of each fraction.

FIG. 2 illustrates the percentage mortality of corn rootworm larvae treated with buffalo grass extract fractions obtained in accordance with the invention using ion exchange chromatography and a High Q Sepharose ion exchange column.

FIG. 3 illustrates the anion exchange chromatographic profile of a buffalo grass extract processed on a High Q Sepharose chromatography column using a Bio-Cad workstation.

FIG. 4 illustrates the gel filtration profile of the Unbound fraction obtained from the anion exchange chromatograph illustrated in FIG. 3.

FIG. 5 is the mass spectrograph of gel filtration fraction "D" illustrated in FIG. 4, which fraction contains the active buffalo grass insecticidal compound.

FIG. 6 illustrates the mass spectrum of the buffalo grass extract gel filtration Pool D fraction.

FIG. 7 illustrates the mass spectrum of the buffalo grass extract gel filtration Pool D fraction after digestion with Proteinase K.

DETAILED DESCRIPTION OF THE INVENTION

References

The teachings of the following patents and publications are incorporated herein by reference.

1. H. D. Belitz et al., *Z. Lebensm. Unters.-Forsch* 174:442–446 (1982).
2. J. T Christeller et al., *Insect Biochem.* 19: 233–241 (1989).
3. V. A. Hilder et al., *Nature* 330: 160–163 (1987).
4. R. Johnson et al., *Proc. Natl. Acad. Sci.* 86:9871–9875 (1989).
5. U. K. Laemmli, *Nature* 227: 680–685 91970).
6. T. H. Czapla and B. A. Lang, *J. Econo Ento.* 83 (6): 2480–2485 (1990).

Terminology and Abbreviations 1. pI=the pH of a solution containing a molecule at which there is no charge on that molecule.
2. IEF=Iso-electric focusing.
3. SDS-PAGE=Sodium dodecyl sulfate—Polyacrylamide gel electrophoresis.
4. NaOAc=sodium acetate
5. Tris-Cl=Trizma based molecular biology reagent.
6. FPLC=HPLC (high pressure liquid chromatography).
7. DTT=Dithiothreitol
8. EDTA=Ethylenediamine tetraacetic acid.
9. BAA=Transit peptide from barley alpha-amylase.

The data and descriptions presented herein are for the purpose of describing the invention and are not to be taken as limiting. It is within the scope of this invention that those skilled in the art, using the teachings herein, will be able to extract, purify and isolate from other plant species the extracted buffalo grass insecticide compound(s), or mixture thereof, described herein if such plants contain said insecticide compound(s).

The insecticidal substance(s) extracted from buffalo grass are believed to be proteinaceous substances; or substances which may attach or complex themselves to proteins and may be carried through the various separation techniques together with proteins; or non-protein substances which might be comprised of amino acids. The early molecular weight data indicated that the insecticidal compound(s) contained in a buffalo grass extract had a molecular weight of about 20 kilodaltons or less. As experience was obtained separating the components of a BG extract, it was observed that the molecular weight of the active component(s) began to decrease until a plurality of substances having a molecular weight of less than 8 kDa and then less than 5 kDa were found to have insecticidal properties. This observation, viewed in the light of the separation and identification techniques used herein, leads to the conclusion that the active insecticidal substance or substances may be of relatively low molecular weight; for example, a low molecular weight peptide or a low molecular weight combination of amino acids which readily associate with proteinaceous substances and can be carried through various separation techniques in association with said proteinaceous substances. Alternatively, the active insecticidal substance may be a part of a protein or protein-like substance which is readily cleaved or broken apart, said insecticidal portion thereof being carried intact with one or a plurality of such cleavage parts and maintaining its insecticidal activity. Whichever the case, the important fact is that the active insecticidal substance, or mixture thereof, while of itself believed to have a molecular weight of less than 5 kDa, can associate with protein or protein-like substances to form a substance or a "complex" or a "conjugate" which has insecticidal properties. Such "complexes" have been observed and bioassayed, and they show insecticidal properties. Consequently, as those skilled in the art will recognize from the teachings herein, BG extracts of varying "purity" may be used for insecticidal purposes.

*B. dactyloides*, buffalo grass, seeds were purchased from Frontier Grass Seed Division, Abernathy, Tex. The seeds were ground to a fine powder using a blender, food processor, mill, mortar and pestle, or similar grinding and powdering means. A buffered aqueous extraction solution was separately prepared which is 50 mM Tris-Cl, 2 mM DTT 1 mM EDTA and pH 7.4. The powdered seed was mixed with the buffered extraction fluid, homogenized at 4° C., and incubated at 4° C. with constant stirring for two hours. The incubated homogenate was then filtered through Miro cloth to remove particulate matter. The Miro cloth filtrate was then centrifuged for 25 minutes at 4° C. and the supernatant liquid which contains the BG extract was separated from the particulate matter which was discarded. The centrifuging and separation of the supernatant liquid was repeated twice and was followed by a final filtration through a series of Millipore filters of sequential pore size and order 0.65 µm, 0.45 µm and 0.22 µm. The Millipore filtrate was then dialyzed for 12 hours against 60 liters deionized water. The protein concentration of the resulting crude, dialyzed extract was determined by bichinconolic acid (BCA) protein assay. Bioassays using the crude, dialyzed extract indicated it contained one or a plurality of insecticidal substances (see Table 1, Control at 1200 ppm extract).

Various methods may be used to isolate and characterize the active insecticidal substance or substances contained in a buffalo grass extract. For example, the substance(s) in buffalo grass extracts can be separated using a Bio-Rad Rotofor Isoelectric Focusing apparatus. Using the Rotofor apparatus, a mixture containing extracted BG substances is added to distilled water containing 1.0 %, pH 3–10 Bio-Lyte ampholytes (Bio-Rad). The extracted substances and ampholyte mixture is then placed in the focusing chamber of the apparatus, which has 20 individual compartments, and the instrument operated in accordance with the manufacturer's instructions. Power is applied and an initial pH gradient is formed. The substances within the chamber concentrate near their individual isoelectric points. After about 1 to 4 hours, the voltage has stabilized, and the various substances within the initial sample have been focused at their isoelectric points. The focused substances are then isolated using the Rotofor's system by which the contents of each compartment within the chamber are simultaneously transferred to a separate test tube. After transfer, each sample may then be further characterized as desired.

Several different buffalo grass extracts have been separated using the Rotofor apparatus and various isolated fractions were bioassayed for their impact in CRW larvae mortality. These bioassays indicate high CRW mortality at or near the pH 9.0 fraction, corresponding to a fraction number between 15 and 19. The active substance in the BG extract thus has a pi of about 9.0. Rotofor fraction Nos. 15–19 produced 100% CRW larvae mortality at 12 ppm ±5× using a Bradford assay.

Figure 1:
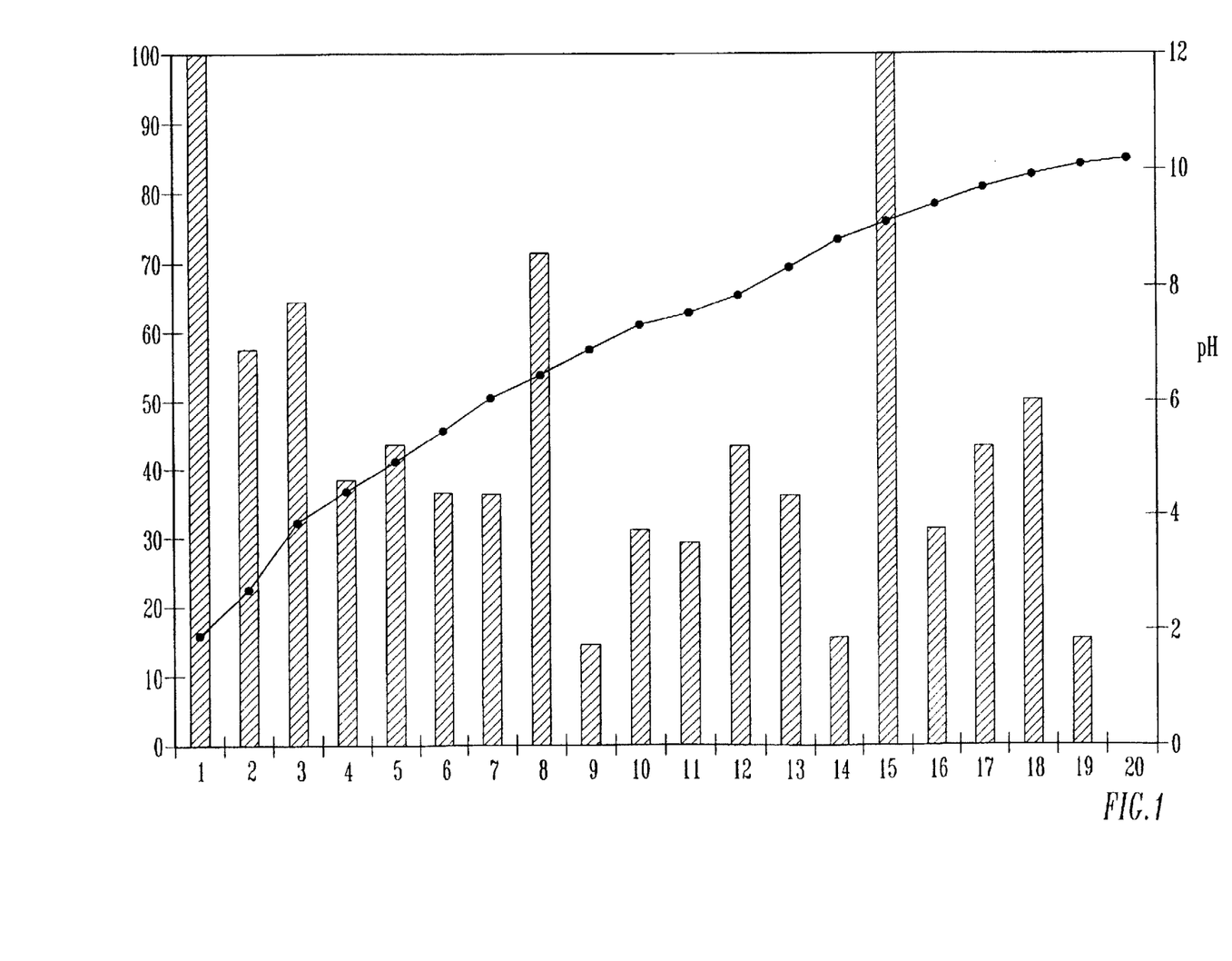

FIG. 1 illustrates the results one may expect from a typical Rotofor separation of a buffalo grass extract. The extract used in a Rotofor separation is filtered through a 0.45 µm filter before use. Typically, a filtrate containing a total of about 15 mg BG substance was used in each separation. After Rotofor separation, the collected fractions were first dialyzed against deionized water which was 1 M in NaCl to remove the ampholyte and then dialyzed against deionized water to remove NaCl. The water-dialyzed fractions were used in bioassays. Three milligrams of crude extract was used as a positive control.

Some buffalo grass extracts were ammonium sulfate precipitated before being subjected to separation using the Rotofor apparatus. Bioassays were performed using both precipitated and unprecipitated Rotofor-separated extracts. Unprecipitated extracts exhibited the 100% mortality described above. In contrast, precipitated extracts showed lower levels of CRW larvae mortality across all Rotofor fractions while maintaining the same overall distribution profile across the fractions. The major difference between the precipitated and unprecipitated samples lies in the region of the acidic fractions, with precipitated acidic fractions 1–3 exhibiting no activity against CRW larvae.

Overall, bioassay results using Rotofor separated fractions indicate that a compound with a pI of 9.0 has excellent activity against CRW larvae, producing 100% mortality at total substance concentrations as low as 12 ppm ±5× in the bioassays.

Figure 2:
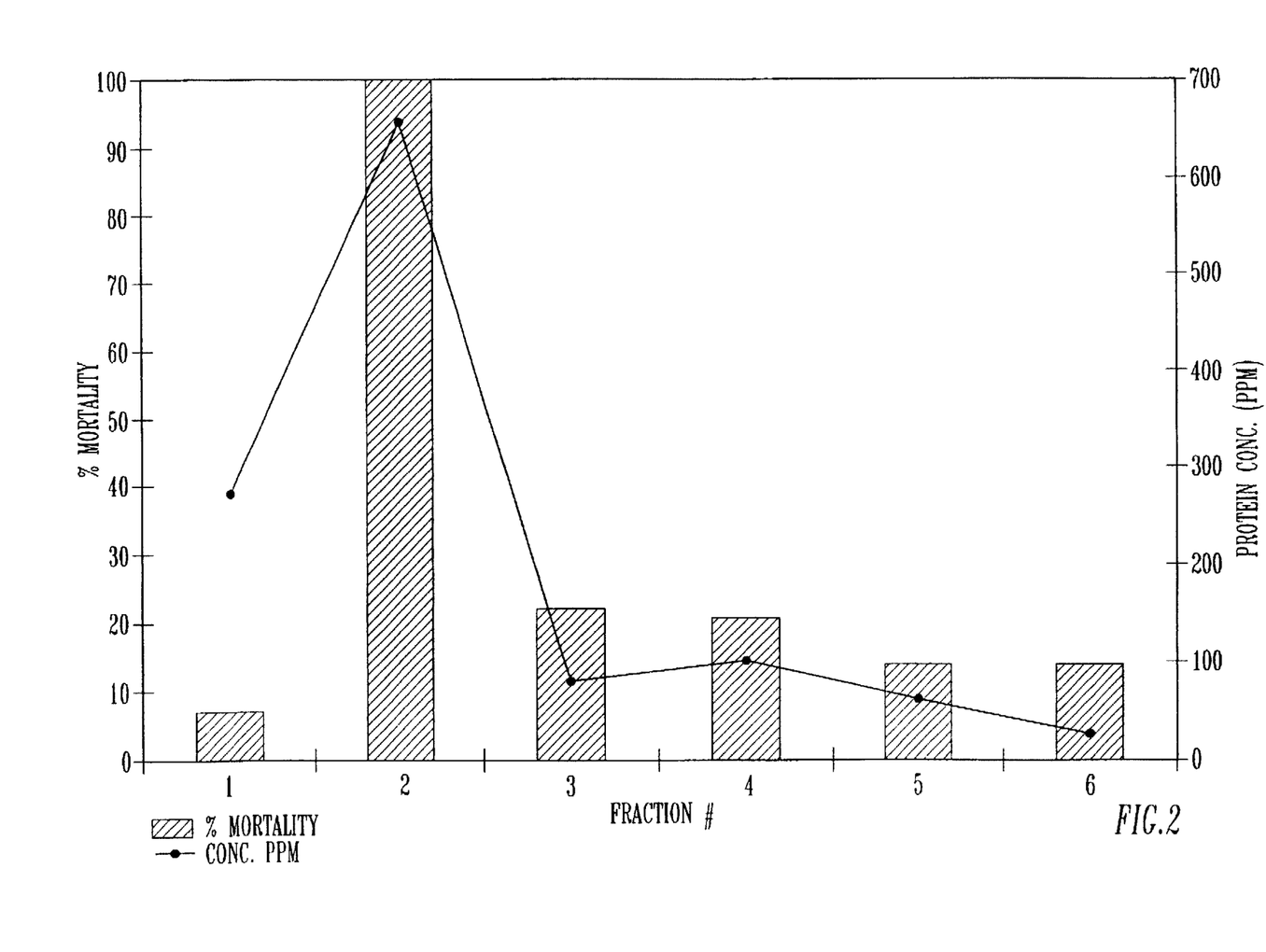

Ion exchange chromatography was used to separate components of a crude buffalo grass extract. FIG. 2 illustrates a typical chromatographic result. As with the Rotofor results, certain fractions, in this case fraction 2, consistently exhibited high levels of CRW mortality in the bioassays. The ion exchange separations were performed using a High Q Sepharose column purchased from Bio-Rad Corporation. Typically, 15 mg of substance, as determined by Bradford assay, was loaded onto the chromatography column. Three milligrams of non-chromatographed extract material was used as control. The profile of the substance was maintained as described above. Fraction 2 from the anion exchange chromatography shows 100% CRW mortality.

SDS-PAGE is used to separate components and determine their molecular weights. The procedure was carried out according to the method of Laemmli (5) using a 10–20% gradient acrylamide gel. BG samples were denatured by boiling for three minutes in SDS buffer (BioRad) which is 2 mM in 2-mercaptoethanol. Bands of material were detected by staining with Coomassie Brilliant Blue R-250 (CBB R-250).

The initial SDS-PAGE separations yielded plates showing bands at 12, 18, 27, 33–35 and 40 kilodaltons. The major component was the 18 kDa band, and all the remainder were relatively minor. Gel filtration chromatography of the bulk BG sample produced a single major peak of 18–20 kDa mass which exhibited insecticidal activity. Subsequent experiments, designed to isolate single components, produced SDS-PAGE results which indicated the active insecticidal substance(s) have a molecular weight less than 20 kDa and probably less than 8 kDa. As a result, numerous experiments were performed to determine the best method of separating the active substance(s).

After numerous experiments, chromatography has been found to be the best method for separating the components of a crude, dialyzed buffalo grass extract. In particular, it was determined that the active substances in a BG extract are best separated by anion exchange chromatography followed by gel filtration or exclusion chromatography. The following paragraphs describe the best method of separation.

The anion exchange chromatography was performed on a Bio-Cad workstation using HQ [HQ=High Q Sepharose] resin (Perceptive Systems). A crude, dialyzed buffalo grass extract was placed on the column and purified by a series of pH 8.5, NaCl buffer solutions prepared in situ by the workstation from:

(1) a buffer of Bis-Tris Propane (pH 6.0), Bis-Tris-Propane (pH 9.0) and deionized water which are combined by the workstation to yield a buffer of pH 8.5 and 10 mM in Bis-Tris-Propane, and (2) 3M NaCl added by the workstation to (1) in an amount sufficient to yield an eluting solution having sequential NaCl concentrations in the range 0.0–1.0M.

Figure 3:
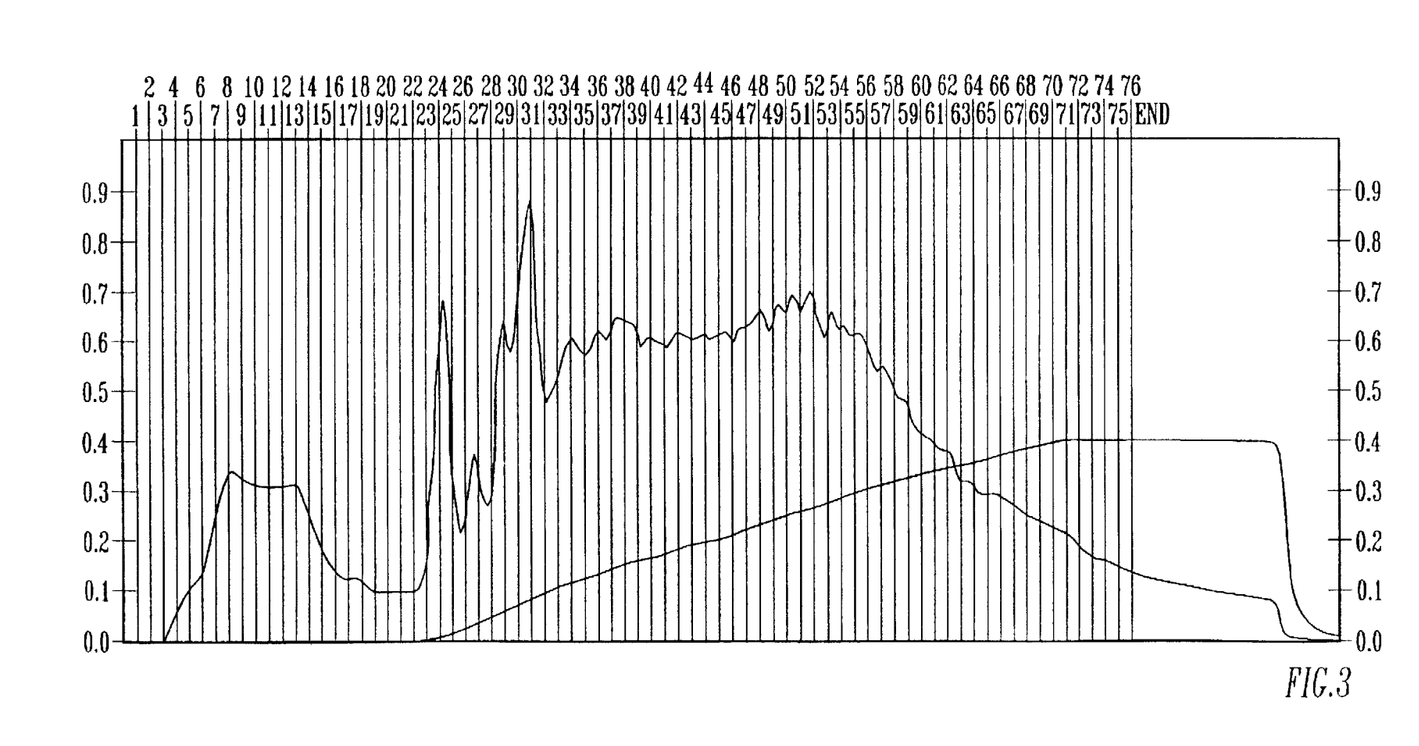

The anion exchange profile is shown in FIG. 3. Samples were collected from the column as 1 ml fractions and were pooled on the basis of their UV absorbance spectra at 280 nanometers (nm). The pooled fractions are designated Unbound (UB, containing fractions 1–22) and Bound (B, containing the remaining fractions) on the basis of the fact that the majority of the active material, the Unbound fraction, is carried through the column by the solvent of the dialyzed extract solution which was loaded onto the column. The Unbound and Bound pools were subsequently extensively dialyzed against deionized water, lyophilized and re-solubilized in deionized water. The protein concentration of the final solution was determined by BCA assay.

Figure 4:
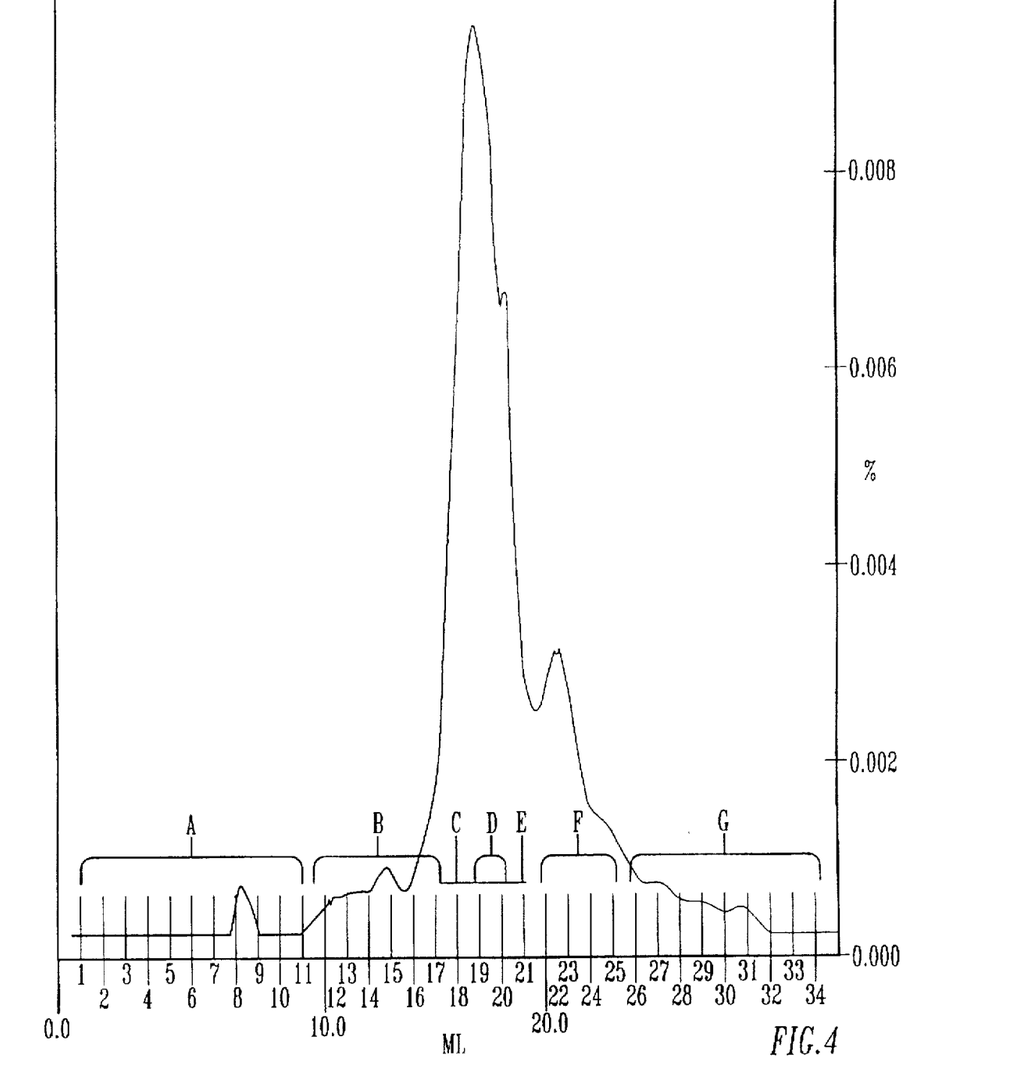

The Unbound pool was further purified by gel filtration or exclusion chromatography, illustrated by FIG. 4, on a Superdex 75 column (Pharmacia, Paramus, N.J.) using pH 7.4 phosphate buffered saline (PBS) solution. Fractions were collected and combined into different pools based on their SDS-PAGE chromatographic profile using 10–20% gradient gel under reducing conditions. The pooled material was then dialyzed against deionized water, lyophilized and resolubilized in deionized water. The concentration of the active substance(s) in the final solution was determined by BCA assay. The various pools comprised the following fractions:

| Gel Filtration Chromatography | |
| --- | --- |
| Pool | Fractions |
| A | 1–10 |
| B | 11–16 |
| C | 17 |
| D | 18–19 |
| E | 20 |
| F | 21–23 |
| G | 24–end |

The active insecticidal substance(s) were primarily found in Pool "D".

Figure 5:
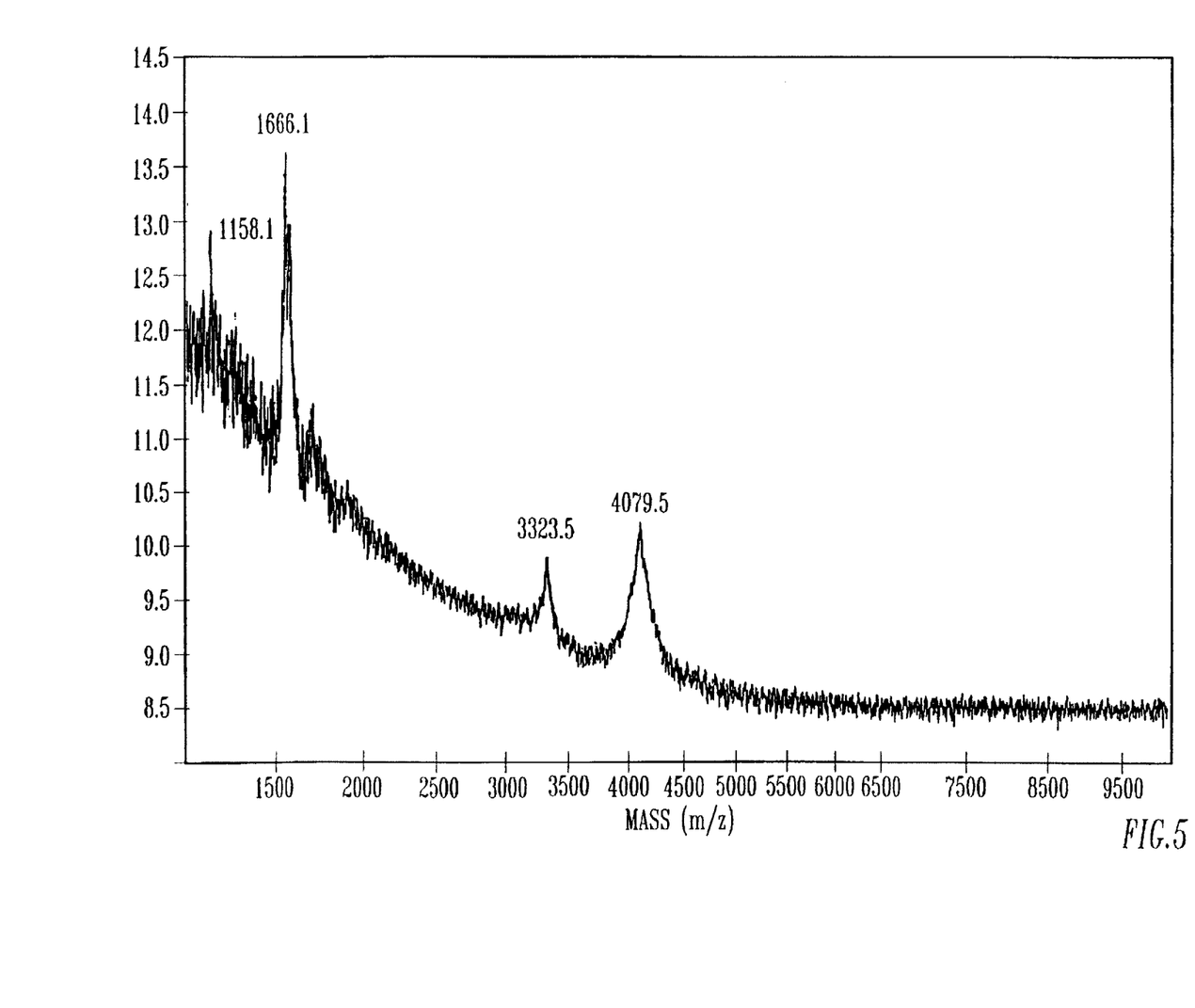

FIG. 5 is an early mass spectrograph of the organic compounds contained within Pool D. The active insecticidal compound extracted from buffalo grass was found to have a molecular weight less than 8 kDA. The mass spectrum in FIG. 5 shows a peak in the range 4050–4100 mu (mass units) (hereafter the 4100 peak) which is believed to correspond to the parent compound. The peak in the range 3300–3350 (hereafter the 3300 peak) may be either a second insecticidal compound or a daughter compound derived from fragmentation the 4050–4100 parent species. [Note: one mass unit (mu) and one dalton are approximately equal.]

Figure 6:
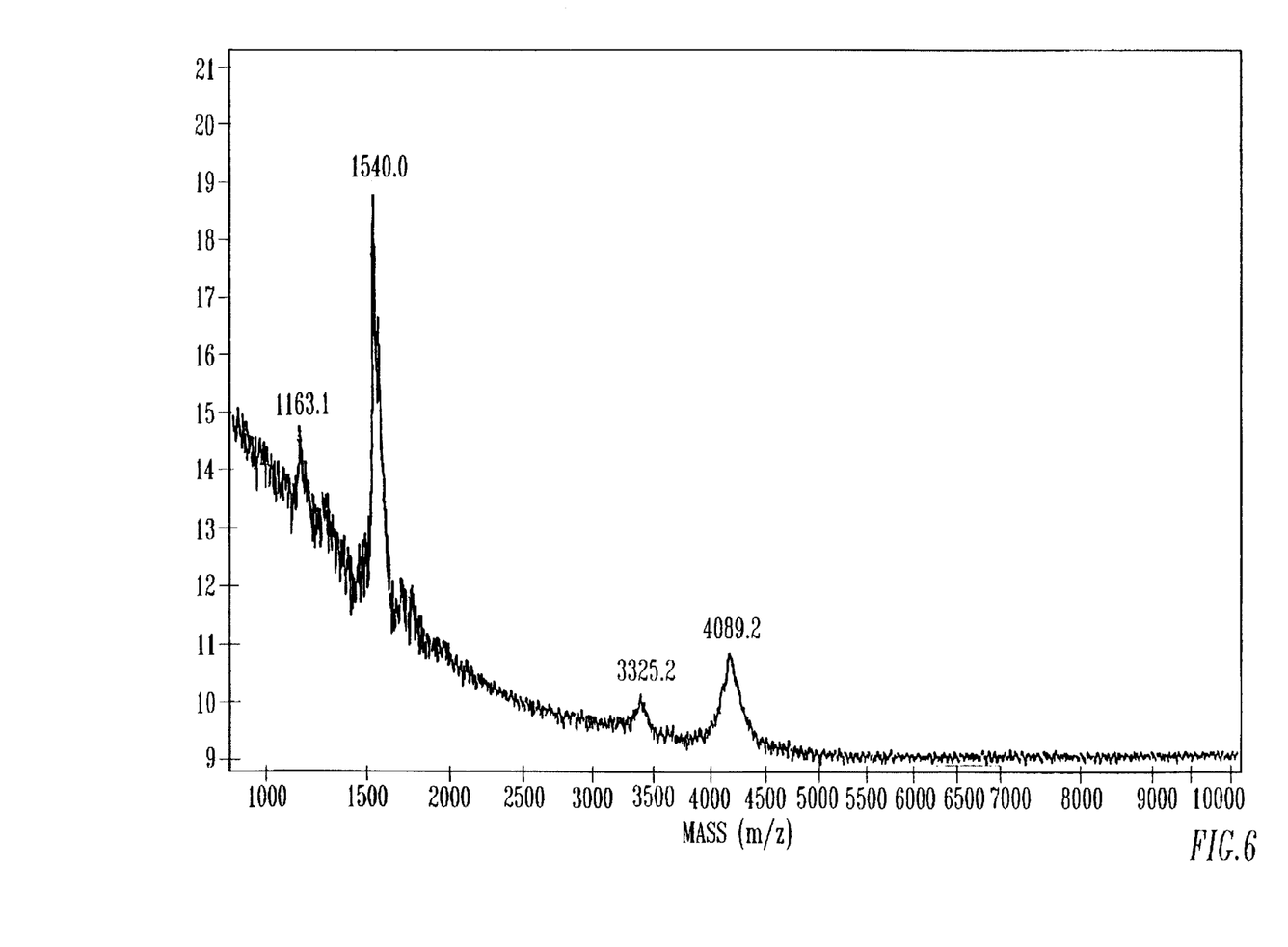

The best method of separating the BG extract substances was repeated a plurality of times, and additional chemical, mass spectral and amino acid analyses and experiments were performed. In all separations, Pool D, as described above, was found to contain the active insecticidal substance. FIG. 6 illustrates a second mass spectral analysis, in water, of Pool D and shows four peaks at about 4089 (hereafter the 4100 peak), 3325 (hereafter the 3300 peak), 1540 (hereafter the 1500 peak) and 1163 mass units. The first three have been determined to be active insecticidal substances. The 1163 peak remains unknown. It may be an as yet unidentified insecticidal substance, a background material or a matrix-derived material.

As a result of the mass spectral experiments, the substances in Pool D were treated with trifluoroacetic acid (TFA). TFA is used to purify peptides by reverse phase chromatography and is also used in amino acid sequence analyses by Edman degradation. A mass spectrum of the BG Pool D extract in 100% concentrated TFA showed no peaks greater than about 250–300 mass units, indicating either complete degradation of the active substance(s) or a masking of a normal mass spectrum. This experiment was performed because normal Edman degradation sequence analyses are done using 100% TFA.

The Pool D extract was then incubated in buffer solutions of pH 2–7 using acetic acid, formic acid, hydrochloric acid, ammonium hydroxide and 100% TFA (as control). Following incubation, mass spectra were obtained for each sample. With the exception of the TFA incubated sample, all showed mass spectra similar to that of FIG. 5.

Subsequent to the TFA experiments, Pool D extract was digested with Proteinase K, a non-specific enzyme used to digest proteins for the purpose of determining whether or not an unknown active substance is a proteinaceous substance. The digestion typically reduces a protein down to its amino acid components. If the substance under investigation was not active after digestion with Proteinase K, it was a protein. If the substance remained active after digestion with Proteinase K, it was likely not a protein although it might still have been composed of amino acids.

Figure 7:
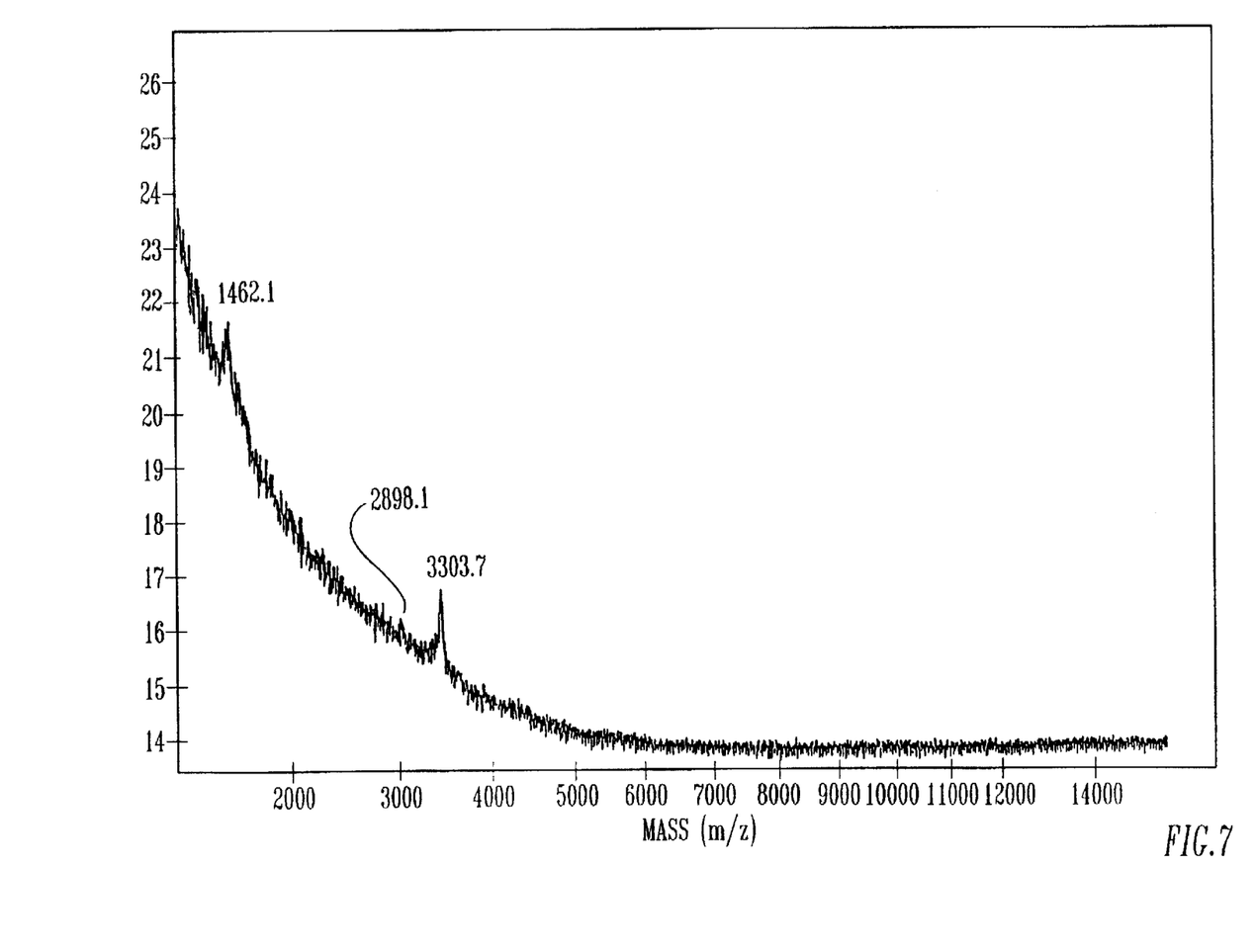

Pool D extract was digested using Proteinase K. The digested material was analyzed by mass spectroscopy and was bioassayed. The mass spectrum is shown in FIG. 7. In comparison to FIG. 6, the 4100 mass units peak has disappeared, and the peaks at approximately 3300 and 1500 mass units remain. The bioassay indicated that the Proteinase K digested extract has insecticidal activity.

Pool D extract was also first digested with Proteinase K and then incubated with 0.1% TFA. The resulting material was analyzed by mass spectroscopy and was bioassayed. The mass spectrum (not shown) is similar to that of FIG. 7, showing the peaks at approximately 1500 and 3300 mass units. The 4100 mass units peak is gone. The product was an active insecticide.

Amino Acid Composition Data

The amino acid components of Pool D buffalo grass extracts were determined as unknowns by two independent laboratories. The results, rounded to the nearest integral value, are given in Table 1. The molecular weight of the insecticidal substance has been estimated based on the amino acid content as shown in Table 1. Table 1 also contains the molecular weights as calculated by the analytical laboratories based on the analyses performed. These values compare favorably with the mass spectral values given above.

TABLE 1

Amino Acid Analysis of BG Extract Pool D.

| Amino Acid | Analysis N. 1 | Analysis No. 2 |
|---|---|---|
| Cys-Acid | 0 | 0 |
| Cys | 0 | 0 |
| Asx[1] | 7 | 7 |
| Thr | 2 | 2 |
| Ser | 2 | 2 |
| Glx[2] | 11 | 12 |
| Pro | 2 | 2 |
| Gly | 3 | 4 |
| Ala | 2 | 2 |
| Val | 1 | 1 |
| Met | 0 | 0 |
| Ile | 1 | 1 |
| Leu | 1 | 1 |
| Tyr | 0 | 0 |
| Phe | 0 | 0 |
| His | 1 | 0 |
| Lys | 1 | 1 |
| Trp | 0 | 0 |
| Arg | 0 | 0 |
| Total Amino Acids | 35–36 | 36–37 |
| Approx. Mol. Wt. (Amino Acids)[3] | 4162–4309 | 4214–4331 |
| Mol. Wt. (actual analyses)[4] | 4099 | 4080 |

Notes:
[1]Asx = aspartic acid + asparagine (aspartic acid amide).
[2]Glx = glutamic acid + glutamine (glutamic acid amide).
[3]These molecular weight ranges are based on the integral amino acid numbers given in Table 1.
[4]These molecular weights were determined by the laboratories performing the amino acid analysis and include partial amino acid species.

Biological Assays

An initial series of bioassay tests were conducted using extracts subjected to acetone precipitation, heat treatment, ammonium sulfate precipitation and separation using Amicon Centripreps. The bioassays continued to show strong insecticidal activity as exhibited by high corn rootworm (CRW) larvae mortality. As a result, an additional series of tests were run to identify the active compound or compounds in the buffalo grass extracts.

The bioassays were performed using neonate insect pests reared on artificial diets containing BG extracts, either crude or purified as taught herein, which were either topically applied to the diet surface or incorporated into the diet as taught by Czapla and Lang (6). The multi-well or multi-cell culture tray used in the bioassays was divided into treatment groups. One or a plurality of control substances, buffalo grass extracts or components of an extract were screened in each tray; each control, extract or component being used in a plurality of tray cells containing diet medium. Each cell was infested with one corn rootworm neonate larva. A Mylar film with ventilation holes was affixed to the top of each tray to prevent the larvae from escaping.

For the topical assays, the subject BG compound or mixture containing the compound was prepared in 0.1M phosphate buffered saline (PBS) buffer (pH 7.8) as a 2% solution. Seventy-five microliters of solution were pipetted onto Stoneville medium in each cell. The culture tray was rotated to ensure equal distribution of the inhibitor. The cells were infected and sealed as described above. The control was either 75 μof 0.1M PBS per cell or another substance as described in the Tables.

For the diet incorporation assays, Stoneville medium was prepared in standard fashion but with only 90% of the prescribed water. The buffalo grass substance(s) or mixture containing the substance(s) was added such that the amount in the diet was in the range of 1–5 μg/g. The control treatment consisted of 0.9 ml PBS buffer, or other substance as described in the Tables, added to 8.1 g of medium. The medium was poured into the cells and the cells were then infested and covered as described above. Mortality and, where applicable, insect weights (Wt., Mean Wt. or Avg. Wt.) were determined at a specified day.

EXAMPLE 1

Buffalo grass was extracted as described above, and the extract chromatographed using anion exchange chromatography, a Bio-Cad workstation and buffered NaCl solutions as described above. Materials coming off the column were collected and pooled on the basis of their UV spectra at 280 nm. The first sample collected was the Unbound (UB) material, comprising extract which was not absorbed by the column. Subsequently, two pools of material which were absorbed and then eluted from the chromatography column were collected and designated Pools I and II (PI and PII).

A bioassay as described above was conducted using topically applied protein from UB, PI and PII. The control was filtered, but unchromatographed, buffalo grass extract. Table 2 gives mortality for the different pools of BG protein at Day 7.

TABLE 2

Insect Mortality

| Pool No. | Protein (ppm) | Mortality |
|---|---|---|
| Control | 1200 | 100% |
| UB | 432 | 100% |
| PI | 96 | 100% |
| PII | 96 | 56% |

The data indicates that the Unbound material and the PI material have high insecticidal activity.

EXAMPLE 2

The data in Table 3 were obtained using southern corn rootworm neonate larvae raised on medium treated with crude buffalo grass extract which had been dialyzed against water using a 3500 molecular weight cutoff (MWCO) membrane. Material below 3500 molecular weight was discarded. The retained material was then separated by size using Centiprep MWCO tubes of sizes shown in Table 3. Similar data was obtained using western corn rootworm. The control was larvae which were raised on medium containing no buffalo grass extract. The test data indicates that buffalo grass contains one or a plurality of substances which are effective insecticides against corn rootworm.

TABLE 3

| Insect Mortality and Weight | | |
|---|---|---|
| Treatment Material | % Mortality | Mean Wt. (mg) |
| Control | 0 | 2.3 |
| 3500 MWCO | 100 | — |
| 6–8000 MWCO | 100 | — |
| 12–14000 MWCO | 80 | 0.9 |

Note:
Weight and mortality determined at day 7.

EXAMPLE 3

Pools C, D and E from the gel filtration illustrated in FIG. 4 and various other substances as described below in Table 4 were used in a bioassay to determine their effect of corn rootworm larvae mortality. The various substances were incorporated into Stoneville medium as described herein. Each test well contained Stoneville diet and one larva. The results were determined after the larvae had fed on the various diets for 7 days.

The BG substance or protein assay used with this bioassay is known to overestimate the substance or protein by five- to ten-fold. Consequently, the true ppm substance or protein added to the diet ranges from about 27 to 40 ppm.

TABLE 4

| Bioassay Using Selected FIG. 4 Material. | | | | | |
|---|---|---|---|---|---|
| Diet | PPM Added | Number Samples | Number Dead | Percent Mortality | Percent Wt. Loss |
| DIRO-1 | — | 28 | 0 | 0 | 0 |
| $H_2O$ | — | 28 | 8 | 29 | 50 |
| Control | 600 | 40 | 32 | 80 | 76 |
| C | 200 | 28 | 10 | 36 | 14 |
| D | 200 | 28 | 24 | 86 | 86 |
| E | 137 | 28 | 20 | 71 | 54 |

Notes:
1. DIRO-1 = Diro Water.
2. $H_2O$ = Laboratory tap water.
3. Control = Crude, dialyzed extract after Millipore filtration.
4. C = Pool C from gel filtration.
5. D = Pool D from gel filtration.
6. E = Pool E from gel filtration.

EXAMPLE 4

Pool D material from a gel filtration was digested with Proteinase K, and the digestion material was bioassayed. Controls were undigested Pool D material, Proteinase K (only) in buffer and 50 mM Tris-Cl in buffer. Fourteen (14) larvae were used for each of the four substances tested. The test was conducted over 7 days using low-melt agarose and 2.5 ml diet to which the test substance was topically applied. The results indicated that Proteinase-digested Pool D material retains its insecticidal properties even after the material having a mass spectral peak at about 4100 mass units has been removed by Proteinase K digestion. This suggests that there is a minimum of two insecticidal substances present in a crude BG extract and that these substances may be capable of combining or complexing with each other to form higher molecular weight species which retain their insecticidal properties. In addition, when these results are combined with the various separation and bioassay data reported herein, the results further suggest that these substances, alone or in a combined form, can combine or complex with other molecules, for example, proteins or peptides, to form insecticidal substances having molecular weight up to approximately 20 kDa.

TABLE 5

| Bioassay Using Proteinase K Digested Pool D BG Extract. | | | |
|---|---|---|---|
| Sample | Amount, ppm | % Mortality | % Wt. Loss |
| Pool D | 200 | 93 | 86 |
| Pool D = Pro. K | 200 | 93 | 74 |
| Pro. K (only) | 10 | 7 | 10 |
| Tris-Cl | — | 0 | 18 |

Other Grasses Having Substances With Insecticidal Properties

Preliminary investigations has shown that other members of the grass family, Poaceae (Griaminae), contains a substance or substances of less than 20 kDa weight which exhibit insecticidal properties. These preliminary investigations, mainly physical separation methods and SDS-PAGE, indicate that the active component(s) may be similar if not the same as those isolated from buffalo grass. Examples of other such members of the grass family Poaceae (Graminae) include:

(1) Food crop grasses such as *Avena sativa* (oats), Hordeum (barley), *Oryza sativa* (rice), Saccharum (sugarcane), *Secale cereale* (rye), *Setaria italica* (millet), *Sorghum bicolor* (sorghum), Triticum (wheat) and *Zea mays* (corn);

(2) Shelter grasses such as Bambusa (bamboo);

(3) Fodder grasses such as Agrostis (bentgrass), Dactylis (orchard grass), Phleum (timothy), Setaria (foxtail grass), Sorghum and *Zea mays;*

(4) Lawn turf grasses such as Agrostis, Cynodon (Bermuda grass), Festuca (fescue grass), Poa (bluegrass), Stenotaphrum (St. Augustine grass), and Zoisia (zoysia grass).

The above list of grasses have one or more substances with insecticidal properties, which substances are believed to be similar to that isolated from buffalo grass. The above list is further believed not to be inclusive of all such grasses. It is believed to be within the scope of this invention that those skilled in the art, using the teachings and suggestions presented herein, should be able to screen other grasses for such insecticidal substances and to isolate such substances for use as insecticides.

A variety of grasses were evaluated for their insecticidal properties. Crude extracts were obtained and evaluated using CRW larvae according to the procedures described herein. A standard seven (7) day mortality test was conducted and the results are presented in Table 6. In Table 6, "++" signifies 100% insect mortality within seven days, "+" signifies 75% within seven days and "24 hrs." signifies 100% mortality within twenty-four hours after the CRW was placed on a diet containing the indicated extract.

TABLE 6

| Crude Grass Extracts Tested Against CRW | | | |
|---|---|---|---|
| Common Name | Genus | Species | Bioassay Result |
| Buffalo Grass | Buchloe | *dactyloides* | ++ |
| Big Bluestem | Andropogon | gerardi | 24 hrs. |

TABLE 6-continued

Crude Grass Extracts Tested Against CRW

| Common Name | Genus | Species | Bioassay Result |
|---|---|---|---|
| Indian Grass | Sorghastrum | avenaceum (new) nutans (old) | 24 hrs. |
| Kleingrass | Panicum | colartum | + |
| Sand Lovegrass | Eragrostis | trichodes | + |
| Blue Grama | Bouteloua | gracilis | 24 hrs. |
| Side Oats Grama | Bouteloua | curtupendula | 24 hrs. |
| Green Spranletop | Leprochloa | dubia | ++ |
| Tall Fescue | Festuca | elatior (new) arundinacea (old) | ++ |
| Sand Bluestem | Andripogon | hallii | 24 hrs. |
| Plains Bristlegrass | Setaria | macrostachya | ++ |
| Little Bluestem | Andropogon | scoparius | 24 hrs. |
| Switchgrass | Panicum | virgatum | ++ |
| Wheatgrass | Agropyon |  | + |
| Alkali Sacuton | Sporodolus | airoides | + |
| Lovegrass | Eragrostis |  | + |
| Corn | Zea |  | ++ |

The data in Table 6 clearly indicates that an extract obtained from each of the indicated grasses contains one or a plurality of substances which have insecticidal activity against CRW.

Those skilled in the art of plant genetics, using the genetic techniques which have been developed over the last several decades, can transfect the genes encoding for the production of the active buffalo grass insecticidal substance(s) identified herein into the genetic code of food crops such as corn, soybeans, squashes, and similar food crops. Expression of the gene encoding the active buffalo grass substance(s) will enable such food crops to produce the insecticide substances and thus protect themselves against attack by insect pests such as those described herein. Methods for producing transgenic plants are well known to those skilled in the art. For example, one may use, among others known to those skilled in the art, the teachings of Koziel et al., BIO/TECHNOLOGY 11: 194 200 (1993), Vaeck et al., Nature 327: 33–37 (1987), Hilder et al., Transgenic Research 4: 18–25 (1995) and Nature 330: 160–167 (1987), and Johnson et al., Proc. Natl. Acad. Sci. 86: 9871–9875, all of which are incorporated herein by reference.

We claim:

1. A composition comprising at least one substance suitable for use as an insecticide and obtained from Buchloe dactyloides by the steps comprising extracting seeds from said Buchloe dactyloides with an aqueous solution to obtain a crude extract having insecticidal properties and purifying the crude extract using separatory techniques to obtain at least one substance with insecticidal properties, which substances has a molecular weight of less than 20 kDa.

2. The composition in accordance with claim 1 wherein said substance has a molecular weight of less than 8 kDA.

3. The composition in accordance with claim 2 wherein said substance has a molecular weight less than 5 kDa.

4. The composition in accordance with claim 3 wherein said substance has a molecular weight of approximately 4100, 3300 or 1500 daltons as determined by mass spectroscopy.

5. A process for protecting plants against insect attack comprising exposing said insects on said plants to a composition comprising an effective amount of at least one insecticidal substance extracted from Buchloe dactyloides, said substance having a molecular weight less than 20 kDa.

6. The process for protecting plants against insect attack in accordance with claim 5 wherein said substance has a molecular weight less than 8 kDa.

7. The process for protecting plants against insect attack in accordance with claim 6 wherein said substance has a molecular weight less than 5 kDa.

8. The process for protecting plants against insect attack in accordance with claim 7 wherein said substance has a molecular weight of approximately 4100, 3300 or 1500 daltons as determined by mass spectroscopy.

9. A process for protecting plants against insect attack, said process comprising the steps of:

(a) extracting buffalo grass seed with an aqueous buffer solution and filtering the extract to remove particulate matter to obtain a composition containing at least one substance having insecticidal properties;

(b) subjecting the composition of step (a) to ion exchange chromatography followed by gel filtration chromatography to obtain a composition containing at least one substance having insecticidal properties, said substance having a molecular weight less than 8 kDa; and (c) applying an effective amount of a composition containing the buffalo grass extract obtained from step (a) or step (b) to a plant to thereby protect said plant against insect attack.

10. A composition comprising at least one substance suitable for use as an insecticide and obtained from Buchloe dactyloides by the steps comprising extracting seeds from said Buchloe dactyloides with an aqueous solution to obtain a crude extract having insecticidal properties and purifying the crude extract using separatory techniques to obtain a substance with insecticidal properties, which substance has a molecular weight of less than 20 kDa; and said substance having an active insecticidal component with an amino acid analysis approximately comprising the following type and number of amino acids: Aspartic acid plus Asparagine=7; Thr=2; Ser=2; Glutamic acid plus Glutamine=11–12; Pro=2; Gly=3–4; Ala=2; Val=1; Ile=1; Leu=1; His=0–1;and Lys=1.

* * * * *

UNITED STATES PATENT AND TRADEMARK OFFICE
CERTIFICATE OF CORRECTION

PATENT NO. : 5,783,190
DATED : July 21, 1998
INVENTOR(S) : Thomas H. Czapla, Scott A. Mundell, and Nandha Kumar Balasubramanian It is certified that error appears in the above-identified patent and that said Letters Patent is hereby corrected as shown below:

On the title page, item [54] and Column 1;

Line [54]
 BUCHLOE DACTYLOIDES EXTRACTS HAVING

Column 13, Line 52
 stance has a molecular weight of less than 20 kDa.

Signed and Sealed this

Fifteenth Day of December, 1998

*Attest:*

BRUCE LEHMAN

*Attesting Officer*　　　　*Commissioner of Patents and Trademarks*